United States Patent [19]

Van Baush

[11] 4,256,476

[45] Mar. 17, 1981

[54] LOW TEMPERATURE PROCESS FOR THE RECOVERY OF ETHANE FROM THERMAL HYDROCRACKING VENT GASES

[75] Inventor: Edward H. Van Baush, Miami, Fla.

[73] Assignee: Hydrocarbon Research, Inc., Lawrenceville, N.J.

[21] Appl. No.: 36,220

[22] Filed: May 4, 1979

[51] Int. Cl.³ .............................................. F25J 3/06
[52] U.S. Cl. ......................................... 62/23; 62/28
[58] Field of Search ...................................... 62/23–28

[56] References Cited

U.S. PATENT DOCUMENTS

| | | | |
|---|---|---|---|
| 3,373,574 | 3/1968 | Fisher | 62/23 |
| 3,626,705 | 12/1971 | Knapp et al. | 62/23 |
| 3,691,779 | 9/1972 | Meisler et al. | 62/23 |
| 3,796,059 | 3/1974 | Banikiotes et al. | 62/23 |

Primary Examiner—Norman Yudkoff
Attorney, Agent, or Firm—Michael A. Jacobs

[57] ABSTRACT

The present invention provides a method for recovering ethane from a gaseous mixture comprising hydrogen, methane, ethane, and aromatics, comprising subjecting the gaseous mixture to a series of condensing steps to separate the components and flashing the so-obtained ethane to produce a substantially pure ethane product stream.

6 Claims, 1 Drawing Figure

LOW TEMPERATURE PROCESS FOR THE RECOVERY OF ETHANE FROM THERMAL HYDROCRACKING VENT GASES

BACKGROUND OF THE INVENTION

1. Field of the Invention

This invention is directed to a process for producing enriched gases from a vent gas stream which comprises hydrogen, low alkanes, aromatics and alkyl aromatics. More particularly, the present invention relates to a process for recovering ethane from a thermal hydrocracking vent gas, the ethane being suitable for use in an ethylene plant.

2. Description of the Prior Art

In thermal hydrocracking processes such an hydrodealkylation (HDA) which is used for producing benzene from an aromatic-rich feedstock or the modified unit (MBE) that produces benzene, ethane and methane from a feedstock of naphtha or gas oil, there is within the hydrocracking reactor a partial pressure of hydrogen that must be maintained to prevent coking and to sustain the reaction. For this reason, it is necessary to remove from the system the light hydrocarbons formed. This is accomplished either by venting the off-gas, which contains the light hydrocarbons, to fuel gas or, if the overall plant has a short supply of hydrogen, by purifying the off-gas and recycling the hydrogen-rich gas back to the thermal cracking reactor.

The recovery of hydrogen, hydrocarbons (as fuel gas), and aromatics by cryogenic means are known in the art. For example, U.S. Pat. No. 3,622,504 discloses a method for separating heavier hydrocarbons from natural gas by first condensing the hydrocarbons, and then flash-separating the mixture. U.S. Pat. No. 3,628,340 is directed to a process for separating condensable contaminants, such as methane, from a crude hydrogen stream. This process utilizes a series of multipass heat exchangers through which the gas flows for stepwise cooling, with interstage separation of condensates which are expanded and passed in a reverse flow path for autogenous refrigeration. U.S. Pat. No. 3,691,779 discloses a process for producing high purity hydrogen. The process comprises a low temperature refrigeration system operating below 120° R., and an adsorption system operating on an adiabatic pressure-swing principle within the temperature range of 200° to 140° R.

It has been found that ethane can be readily recovered, purified and enriched to a high degree by flashing, heating, and re-condensing between two temperature points that can be readily controlled without external assistance.

Thus, a broad concept of the present cryogenic system is as follows:

(a) Providing a dry cryogenically acceptable feed gas having a pressure between 450 psia to 1000 psia;
(b) Cooling the feed gas through a series of phase separators to recover alkyl aromatics, aromatics, lower alkanes and hydrogen;
(c) Throttling or flashing the hydrocarbon contents to lower pressures to supply the Joule Thompson-type refrigeration; and further throttling the hydrocarbon contents to form a condensate liquid which is rich in ethane.

SUMMARY OF THE INVENTION

According to the present invention, there is provided a process for recovering ethane from an off-gas comprising hydrogen, lower alkanes, aromatics and alkyl aromatics, which process comprises subjecting the off-gas to a series of flashing, phase separation, re-warming and re-cooling to produce a product stream which comprises primarily ethane.

BRIEF DESCRIPTION OF THE INVENTION

The present process for recovering ethane from a gaseous mixture containing hydrogen, alkanes aromatics and alkyl aromatics comprises:

(a) cooling the gaseous mixture to condense the aromatics;
(b) separating the condensed aromatics from the gaseous mixture;
(c) cooling the resulting gaseous mixture to condense the ethane;
(d) separating the condensed ethane from the gaseous mixture of (c);
(e) cooling the gaseous mixture of (d) to condense the methane;
(f) separating the condensed methane from the gaseous mixture which is primarily composed of hydrogen;
(g) recycling the condensed methane and gaseous mixture of (f) for use as coolants in steps (a), (c), and (e);
(h) warming the ethane of (d) to produce a gas-liquid mixture by using the ethane as a coolant in (b);
(i) flashing the gas-liquid mixture of (h) to separate the gas and liquid phases, the methane being in the gas phase and the ethane in the liquid phase; and
(j) recycling the methane and ethane obtained in (i) for use as coolants in steps (a) and (c).

DETAILED DESCRIPTION OF THE INVENTION

Figure 1:
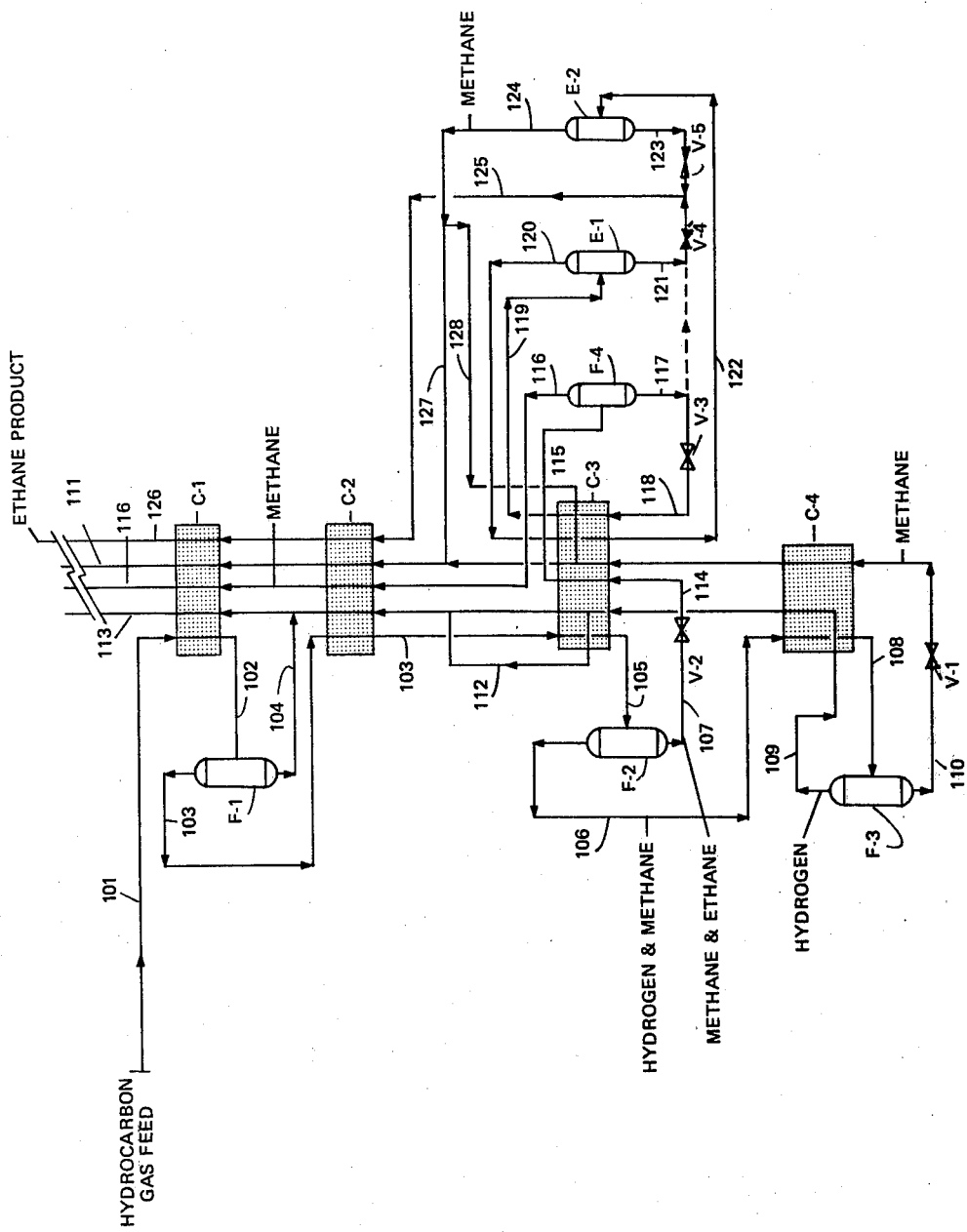
FIG. 1 is the flow sheet for the process shown in the Example.

In accordance with the present invention, a gaseous feed which is the off-gas from a thermal hydrocracking process is fed to the warm end of a first condenser. The gaseous feed generally comprises hydrogen, lower alkanes, aromatics such as benzene, and alkyl aromatics such as toluene and ethylbenzene. Specific examples of lower alkanes include methane and ethane. The gaseous fed usually has a temperature of from about 50° to about 80° F. and a pressure of from about about 700 to about 730 psig. Upon leaving the first condenser, the feed has a temperature of from about −20° to about −60° F., its pressure being substantially unchanged. This cooling step condenses out most of the aromatics contained in the gaseous feed.

The cooled feed stream is then fed to a first phase separator whereby an overhead vapor product containing hydrogen, alkanes (specifically methane and ethane) as well as a bottom liquid product containing primarily all of the aromatics and alkyl aromatics present in the feed stream are obtained. The overhead vapor product from this phase separator is then fed to the warm ends of a second and a third condenser, connected in series, in order to condense the ethane contained therein. The product stream leaving the cold end of the third condenser has a temperature of from about −180° to about −220° F. and a pressure of from about 700 to 720 psig. This product is then fed to a second phase separator to obtain an overhead vapor product containing primarily the hydrogen and methane and a bottom liquid product containing primarily ethane. The overhead vapor product is then fed to the warm end of a fourth condenser to condense the methane. Upon exiting this fourth condenser, the product has a temperature of from about −220° to about −260° F. and a pressure of from about 700 to 710 psig. This product is fed to a fourth phase separator whereby an overhead vapor product comprising about 90% hydrogen and a bottom liquid product comprising primarily methane are obtained. The overhead vapor product containing hydrogen is fed to the cold ends of the fourth, third, second and first condensers, connected in series, to produce a product stream having a pressure of from about 650 to about 750 psig and a temperature of from about 40° to about 60° F. in temperature. In this connection, the liquid bottom product from the first phase separator may be, after throttling, combined with the hydrogen-containing overhead stream from the fourth phase separator when this stream leaves the second condenser. As a result, the product stream leaving the warm end of the first condenser comprises hydrogen and the aromatics originally present feed mixture.

The methane-containing bottom liquid product of the third phase separator is throttled to a pressure ranging from about 25 to about 5 psig. The throttled product is fed to the cold end of the fourth condenser, i.e. countercurrent to the feed stream. The throttled liquid methane vaporizes within the fourth condenser. This methane vapor is then fed successively to the third, second, and first condensers, connected in series, to warm the feed gas so that as it leaves the first condenser, it has a temperature of from about 40° to about 60° F. and a pressure ranging from about 20 to about 1 psig. As the methane vapor stream flows through the latter three condensers, it is joined by other low pressure streams, as specified below, to form a fuel gas stream.

The liquid separated in the second phase separator contains the ethane to be recovered. This stream is throttled to a pressure ranging from 100 psig to 60 psig and fed to the cold end of the third condenser to evaporate off the methane to obtain a liquid which is rich in ethane. The resulting gas-liquid stream is fed to a fourth phase separator to produce an overhead vapor product containing primarily methane and a bottom liquid stream comprising primarily ethane. The overhead vapor product containing the methane is fed to the second and first condensers, connected in series, to warm same to ambient temperature. As the methane stream leaves the present cryogenic process, the pressure ranges from about 95 to about 55 psig. The bottom liquid product, which is rich in ethane, is throttled to a pressure ranging from about 30 to about 10 psig across a suitable throttling valve. As a result of the throttling, this liquid stream drops very low in temperature and may be fed to the cold end of the third condenser as an supplemental coolant. Consequently, the liquid stream is warmed to the operating outlet temperature, thus causing a portion of the liquid stream to vaporize. This gas-liquid mixture, which has a temperature of from about −150° to about −190° F. and a pressure ranging from about 27 to 7 psig, is fed to a first ethane flash drum to produce an overhead vapor product which is primarily methane and bottom liquid product which comprises a very pure liquid ethane. The overhead vapor product, which may still contain some ethane vapor, flows back to the warm end of the third condenser and is once again cooled to the lower temperature of the cold end, condensing substantially all of the ethane contained therein. This cooled product stream is fed to a second ethane flash drum to separate the liquid ethane from the vapor, which is primarily methane. This overhead vapor product joins the methane stream which is fed to the warm ends of the first, second, third, and fourth condensers to produce a product stream comprising methane which, upon leaving the cryogenic recovery process, has a temperature of from about 40° to about 60° F. and a pressure of from about 6 to about 10 psig. The two liquid ethane streams from both of the ethane flash drums are throttled to a pressure of from about 0 to about 6 psig and then combined to form a single product ethane stream. This ethane stream is fed successively to the warm ends of the second and first condensers to warm the stream to a temperature of from about 50° to about 60° F. This stream has a pressure of from about 0 to 5 psig.

In the above described process, the temperature between the second and third condensers is of primary importance in determining the recovery and purity of the ethane product. In other words, the efficiency of the process may be governed by the temperature of the gas-liquid stream leaving the warm end of the third condenser, such stream containing primarily ethane and some methane. Should this stream leave the condenser at too low a temperature, the liquid phase will retain a high proportion of methane which will eventually leave the cryogenic recovery process as a low pressure fuel gas. On the other hand, should this stream leave at too high a temperature, the ethane product may be lost to the high pressure fuel gas system. Moreover, in addition to losing the ethane, the liquid content in the fourth phase separator will be so high in ethane that effective cooling in the third condenser may not be achieved.

Several methods are available for controlling the temperature of the methane-containing stream, mentioned in the preceeding paragraph. Firstly, in the event that the temperature for this ethane-containing stream becomes too cold, some of the cold hydrogen gas product will bypass the warm end of the condenser. This hydrogen bypass gas is taken from the midpoint of the condenser because of the high pressure required on the fuel gas stream. A high pressure requirement imposes a fairly close temperature difference on the cold end of the condenser. As a result, the fullest amount of the cold flow is required at this location. This is particularly true when the feed stream contains a high concentration of ethane.

Secondly, to increase the temperature, the rate of vaporization in the third condenser may be depressed.

Thirdly, a portion of the liquid stream may be bypassed from the bottom of the fourth phase separator to the first ethane flash drum. This will have the effect of reducing the available refrigeration to the third condenser. However, it should be noted that this bypassing operation has the effect of injecting a little more methane into the ethane product stream, thereby decreasing the vaporizing temperature of the ethane product should it become too pure. A higher back pressure would counter this effect.

In the situation where the temperature of the stream exiting the warm end of the third condenser becomes too high, the following corrections may be made. Firstly, cold gas from the second ethane flash drum may be introduced into the third condenser. This stream adds more refrigeration to the condenser, thus causing a decrease in temperature at the warm end.

Secondly, when the effluent temperature at the warm end of the third condenser becomes much warmer than desired, the liquid product flowing from the fourth separator will become high in ethane content, thus depressing the boiling rate thereof. To cure this problem, a portion of the bottom liquid product from the second phase separator may be introduced to the liquid product stream from the fourth phase separator. The introduction of the methane contained in the product from the second phrase separator decreases the temperature of this vaporizing stream. It is noted that this method may also be used in the event that the ethane content in the feed stream raises far above anticipated proportions.

A third method is to lower the fuel gas line pressures. For the case where the ethane product is too pure, thus causing a temperature pinch in the second condenser, liquid methane can be transferred into the ethane product stream to correct this problem.

The following example further illustrates the present invention. However, it must be noted that the example is for illustrative purposes and should not be construed to be limiting.

EXAMPLE

According to the present process, a vent gas (off-gas) 101 is fed to the warm end of first condenser C-1, as shown in the Figure. Feed stream 101 has the following composition, on a parts by volume or mole basis. Unless otherwise specified, all compositions in this example are on a parts by mole basis.

| hydrogen | 1714 |
| methane | 1070 |
| ethane | 325 |
| benzene | .4 |
| toluene | 4.0 |
| ethylbenzene | trace |
| hydrogen sulfide (ppmv) | 4.0 |

This feed stream has a temperature of 65° F. and a pressure of 715 psig. The feed is cooled and leaves condenser C-1 as stream 102, having a temperature of −40° F. and a pressure of 715 psig. Stream 102, which comprises a liquid phase containing primarily condensed benzene, toluene, and ethyl benzene, and a vapor phase which comprises hydrogen, methane and ethane, is fed to phase separator F-1. The overhead vapor product exits phase separator F-1 in stream 103 whereas the bottom liquid product leaves as stream 104. Vapor stream 103 is then fed to the warm ends of condensers C-2 and C-3, connected in series, whereby most of the ethane contained therein is condensed. This stream leaves the cold end of condenser C-3 as stream 105, having a temperature of −200° F. and a pressure of 710 psig. Stream 105 is then fed to phase separator F-2, from which overhead vapor process stream 106 and bottom liquid stream 107 exit. Stream 106 is introduced to the warm end of condenser C-4 and exits therefrom as stream 108, at a temperature of −240° F. and a pressure of 704 psig. Stream 109 comprises the following:

| hydrogen | 1683 |
| methane | 358 |
| ethane | 4.3 |

Stream 108 is then separated into a vapor stream and a liquid stream by means of phase separator F-3. The overhead vapor product from phase separator F-3 exits as stream 109, this stream containing primarily hydrogen. Stream 109 is recycled to condenser C-4 to use as a coolant for stream 106. The liquid stream 110 from phase separator F-3, which stream contains primarily methane, is throttled across valve V-1 and then fed successively, to the warm ends of condensers C-4, C-3, C-2, and C-1 to produce stream 111, having a temperature of 51° F. and a pressure of 8 psig. The overhead vapor product 109 from phase separator F-3 is fed successively to condensers C-4, C-3, C-2 and C-1 to form stream 113 having a temperature of 51° F. and a pressure of 693 psig. Stream 113 has the following composition:

| hydrogen | 1674 |
| methane | 167 |
| ethane | 8 |
| benzene | .4 |
| toluene | 4 |

The bottom liquid product 104 from phase separator F-1 is fed to stream 113 prior to the introduction of the latter to the cold end of condenser C-1. It is noted that part of stream 109 flowing through condenser C-3 may be bypassed around the warm end of the condenser stream 112. This bypass stream may be used for controlling the temperature of the ethane-containing stream leaving the warm end of condenser C-3.

Bottom liquid stream 107 from phase separator F-2 is flashed across valve V-2 to a lower pressure. Thereafter, the throttled liquid 114 is fed to condenser C-3, from which it emerges as stream 115, having a temperature of −170° F. and 98 psig. Stream 115 has the following composition:

| hydrogen | 31 |
| methane | 709 |
| ethane | 313 |
| toluene | 2 |

Stream 115, which comprises a gas-liquid mixture, is fed to phase separator F-4 to produce overhead vapor product stream 116 and bottom liquid product stream 117. Vapor stream 116 contains primarily methane and is fed to condensers C-1 and C-2 to yield stream 117 having a temperature of 51° F. and a pressure of 94 psig. Stream 117 has the following composition:

| hydrogen | 31 |
| methane | 423 |
| ethane | 11 |

Bottom liquid stream 117 from phase separator F-4 is throttled to a lower pressure across throttling valve V-3, from which stream 118 emerges. Stream 118 is then fed to the cold end of condenser C-3, leaving this condenser as stream 119. Stream 119 has a temperature of −170° F. and a pressure of 18 psig and the following composition:

| hydrogen | 3 |
| methane | 286 |

| | |
|---|---|
| ethane | 302 |

Stream 119 is fed to ethane flash drum E-1. The overhead vapor product leaves flash drum E-1 as stream 120 whereas the bottom liquid leaves as stream 121. Vapor stream 120, which still contains some ethane is fed to the warm end of condenser C-3 to condense out the ethane contained therein. This stream leaves condenser C-3 as stream 122 at a temperature of −200° F. and a pressure of 16 psig. The composition for stream 122 is as follows:

| | |
|---|---|
| hydrogen | .3 |
| methane | 240 |
| ethane | 25 |

Stream 122 is fed to ethane flash drum E-2 to produce a bottom liquid stream 123 and an overhead vapor stream 124 which contains primarily methane. Liquid streams 121 and 123 are throttled across valves V-4 and V-5, respectively, and combined to form products stream 125 having a temperature of −182° F. and a pressure of 3 psig. Stream 125 is fed to condensers C-1 and C-2, connected to series, to produce an ethane product stream 126 having a temperature of 51° F. and a pressure of 1 psig. Vapor product stream 124 from ethane flash drum E-2 is divided into stream 127 and 128. Stream 127 is fed to the methane containing stream exiting from condenser C-3 whereas stream 128 is fed to the mid point of condenser C-3. Streams 127 and 128 may be proportioned in order to effect temperature control over stream 115. Alternatively, bypass stream 112 may also be used to control the temperature of stream 115. Streams 127 and 128 are then combined with stream 110 and fed successively to condensers C-1 and C-2 to form stream 111.

What is claimed is:

1. A process for separating ethane from a gaseous feed comprising a mixture of hydrogen, alkanes, aromatics and alkyl aromatics comprising:
    (a) feeding the gaseous feed to a first condenser to condense the aromatics and alkyl aromatics in the feed;
    (b) feeding the product of (a) to a first phase separator to obtain an overhead vapor product and a bottom liquid product which contains substantially all of the aromatics present in the feed;
    (c) feeding the overhead vapor product successively to a second and a third condenser to condense the ethane contained therein;
    (d) feeding the product of (c) to a second phase separator to obtain an overhead vapor product and a bottom liquid product comprising primarily ethane;
    (e) feeding the overhead vapor product of (d) to a fourth condenser to condense the methane contained therein;
    (f) feeding the product of (e) to a third phase separator to obtain an overhead vapor product comprising primarily hydrogen and a bottom liquid product comprising primarily methane;
    (g) feeding the overhead vapor product of (f) successively to the fourth, third, second, and first condensers and combining the bottom vapor product from the first phase separator of (b) with the overhead vapor product of (f) leaving the second condenser to obtain a product stream having ambient temperature and pressure and comprising the hydrogen and the aromatics present in the feed;
    (h) feeding the bottom liquid product from the third phase separator in (f) to the fourth, third, second, and first condensers in succession to obtain a fuel gas stream comprising the methane present in the feed and having ambient temperature and pressure;
    (i) feeding the bottom liquid product from the second phase separator of (d) to the third condenser to heat the liquid to a gas-liquid mixture;
    (j) feeding the gas-liquid mixture of (i) to a fourth phase separator to obtain an overhead vapor product comprising primarily methane and a bottom liquid product comprising primarily ethane;
    (k) throttling the liquid product of (j) and feeding the throttled product of the third condenser to heat the liquid product to form a gas-liquid mixture;
    (l) feeding the gas-liquid mixture of (k) to a first ethane flash drum to obtain an overhead vapor product comprising methane and ethane and a bottom liquid product which is substantially pure ethane;
    (m) feeding the overhead vapor product of (l) to the third condenser to condense the ethane;
    (n) feeding the product of (m) to a second ethane flash drum to obtain an overhead vapor product containing primarily methane and a bottom liquid product containing primarily ethane;
    (o) combining the bottom liquid products of steps (m) and (n) to form a liquid ethane-containing stream and feeding the ethane stream to the second and first condensers in succession to heat the ethane stream to ambient temperature and pressure; and
    (p) combining the overhead vapor product from step (n) with the bottom product of (g) and feeding the combined product to the second and first condensers in succession.

2. The process of claim 1 wherein the temperature of the gas-liquid mixture obtained in step (i) is increased by increasing the amount of overhead vapor product obtained in step (f) which is bypassed around the warm end of the third condenser.

3. The process of claim 1 wherein the temperature of the gas-liquid mixture obtained in step (i) is increased by depressing the rate of vaporization in the third condenser.

4. The process of claim 1 wherein the temperature of the gas-liquid mixture obtained in step (i) is increased by bypassing a portion of the bottom liquid product from the fourth phase separator to the first ethane flash drum.

5. The process of claim 1 wherein the temperature of the gas-liquid mixture obtained in step (i) is decreased by feeding the overhead vapor product from the second ethane flash drum to the warm end of the third condenser.

6. The process of claim 1 wherein the temperature of the gas-liquid mixture obtained in step (i) is decreased by feeding a portion of the bottom liquid product from the second phase separator to the liquid product stream from the fourth phase separator.

* * * * *